(12) United States Patent
Bernard et al.

(10) Patent No.: US 6,506,926 B1
(45) Date of Patent: Jan. 14, 2003

(54) PROCESS FOR THE PREPARATION OF 2-ALKYTHIOBENZONITRILE DERIVATIVES

(75) Inventors: Didier Bernard, Lyons (FR); Alain Truchon, Sathonay Camp (FR)

(73) Assignee: Rhone-Poulenc Agro, Lyons (FR)

( * ) Notice: Subject to any disclaimer, the term of this patent is extended or adjusted under 35 U.S.C. 154(b) by 0 days.

(21) Appl. No.: 09/462,177

(22) PCT Filed: Jul. 3, 1998

(86) PCT No.: PCT/EP98/04948

§ 371 (c)(1),
(2), (4) Date: Mar. 28, 2000

(87) PCT Pub. No.: WO99/02490

PCT Pub. Date: Jan. 21, 1999

(30) Foreign Application Priority Data

Jul. 7, 1997 (GB) ............................................. 9714306

(51) Int. Cl.$^7$ ............................................ C07C 255/49
(52) U.S. Cl. ...................................... 558/378
(58) Field of Search ........................................ 558/378

(56) References Cited

U.S. PATENT DOCUMENTS 5,633,384 A  *  5/1997  Kagano et al. ............. 548/209
5,684,206 A  *  11/1997  Casado et al. .............. 568/336

FOREIGN PATENT DOCUMENTS

| EP | 0418175 | 3/1991 |
| EP | 0527036 | 2/1993 |
| EP | 0705243 B1 | 6/1998 |

OTHER PUBLICATIONS

Harris et al, *J. Medicinal Chemistry*, vol. 33, No. 1, pp. 434–444 (1990).
Beck et al, *J. Organic Chemistry*, vol. 37, No. 21, pp. 3224–3226 (1972).
Coombes et al, *Phosphorus and Sulfur*, vol. 14, No. 2, pp. 139–142 (1983).

* cited by examiner

*Primary Examiner*—Alan L. Rotman
*Assistant Examiner*—Ebenezer Sackey
(74) *Attorney, Agent, or Firm*—Burns, Doane, Swecker & Mathis, L.L.P.

(57) ABSTRACT

A process for preparing a compound of the formula:

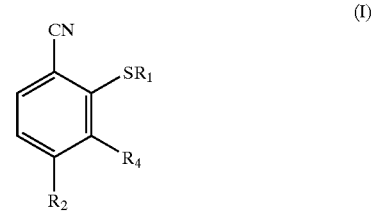

(I)

which comprises reacting a compound of the formula:

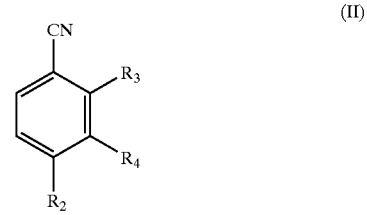

(II)

wherein $R_3$ is nitro or halo, with a compound of formula $R_1S$—X wherein X is hydrogen or alkali metal.

11 Claims, No Drawings

PROCESS FOR THE PREPARATION OF 2-ALKYTHIOBENZONITRILE DERIVATIVES

This application is a 371 of PCT/EP98/04948 filed Jul. 3, 1998.

This invention relates to a process for preparing certain 2-alkylthio substituted benzonitriles, which are useful as chemical intermediates, for example in the preparation of herbicidally active compounds.

2-Alkylthio-substituted benzonitriles are intermediates in the preparation of agrochemicals such as herbicides, for example as described in EP 0527036. It is desirable to provide such compounds in high yields and also to develop new procedures which allow the efficient displacement of 2-nitro or 2-halo substituted benzonitriles to furnish 2-alkylthio substituted benzonitriles.

The present invention seeks to provide a high yielding process for preparing 2-alkylthio substituted benzonitriles.

Thus, the present invention provides a process for preparing a 2-alkylthio-substituted-benzonitrile derivative of formula (I):

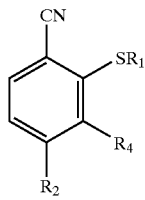

(I)

wherein $R_1$ represents $C_{1-6}$ alkyl;

$R_2$ represents $C_{1-6}$ haloalkyl, $C_{1-6}$ alkyl. $C_{1-6}$ haloalkoxy. $C_{1-6}$ alkoxy. $SO_nR_5$ or halogen;

$R_4$ represents hydrogen, $C_{1-6}$ haloalkoxy, $C_{1-6}$ alkoxy. $SO_nR_5$ or halogen; or a 5 or 6-membered heterocyclic ring (which may be unsaturated or partially saturated) containing 1 to 3 hetero atoms selected from oxygen, nitrogen and sulphur, optionally substituted by halogen, $C_{1-6}$ haloalkyl, $C_{1-6}$ alkyl, $C_{1-6}$ haloalkoxy, $C_{1-6}$ alkoxy, $SO_nR_5$, nitro or cyano;

$R_5$ represents $C_{1-6}$ alkyl; and n represents 0, 1 or 2; which comprises reacting a compound of formula (II):

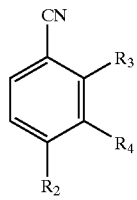

(II)

wherein $R_2$ and $R_4$ are as hereinbefore defined and $R_3$ represents nitro or a halogen atom selected from fluorine, chlorine and bromine, with a compound of formula $R_1S$—X, wherein $R_1$ is as hereinbefore defined and X is hydrogen or an alkali metal.

When $R_4$ represents a heterocyclic ring, preferred rings include 3-isoxazolyl, 5-isoxazolyl, 2-thiazolyl, 5-oxazolyl, 2-furyl, 3-furyl, 2-thienyl and 3-thienyl.

$R_1$ preferably represents methyl.

$R_2$ preferably represents trifluoromethyl.

$R_3$ preferably represents nitro or chlorine.

$R_4$ preferably represents hydrogen.

X preferably represents a sodium, potassium or lithium atom.

In an especially preferred embodiment of the invention $R_1$ represents $C_{1-6}$ alkyl (methyl is most preferred);

$R_2$ represents $C_{1-6}$ haloalkyl (trifluoromethyl is most preferred);

$R_3$ represents nitro or a halogen atom selected from fluorine, chlorine and bromine (nitro or chlorine are most preferred); and $R_4$ represents hydrogen.

The above reaction to prepare compounds of formula (I) by the reaction of a compound of formula (II) with a compound of formula $R_1S$—X may be performed using various solvents such as aromatic hydrocarbons for example toluene or xylene, ethers such as tetrahydrofuran, dioxan or tert-butyl methyl ether; amides such as N,N-dimethylformamide; sulphoxides such as dimethylsulphoxide; or ketones, for example methyl ethyl ketone or acetone. An especially preferred solvent is acetone, optionally in the presence of water. It has been found that the reaction proceeds in excellent yield using these conditions.

A preferred compound of formula $R_1S$—X is sodium thiomethoxide, which may be used in dry solid form or conveniently as a solution in water.

Where X is hydrogen, a base is generally present in the reaction mixture. Examples of suitable bases are alkali metal or alkaline earth metal carbonates, alkoxides or hydrides such as potassium carbonate, potassium t-butoxide or sodium hydride. or amidine bases such as 1,8-diazabicyclo [5.4.0]undec-7-ene or 1,1,3,3-tetramethylguanidine.

The reaction is generally performed at a temperature from about −20° C. to about 120° C. preferably from about 10° to about 60° C. and most preferably from about 10° to about 40° C.

The molar ratio of the benzonitrile derivative of formula (II): alkyl thiol (or metal salt thereof) of formula $R_1S$—X is generally from about 1:1 to about 1:4, preferably from about 1:1 to about 1:2.5 and most preferably from about 1:1 to about 1:1.2.

Optionally the reaction may be performed in a two phase system consisting of water and another solvent which has low solubility in water, in the presence a phase transfer catalyst. Examples of phase transfer catalysts which are suitable include ammonium salts such as tetrabutylammonium chloride; phosphonium salts such as tributylhexadecylphosphonium bromide; guanidinium salts such as hexaethylguanidinium chloride or hexamethylguanidinium chloride; or crown ethers such as 18-crown-6. Suitable solvents for use with water and the phase transfer catalyst include aromatic hydrocarbons for example toluene or xylene, ethers such as tert-butyl methyl ether, halogenated solvents such as chlorobenzene or dichloromethane, generally employed in admixture with water. The quantity of phase transfer catalyst employed is generally from a 2 to 10% molar ratio (relative to the molar amount of compound of formula (II)). When conducted under these conditions the reaction is generally carried out at a temperature of from about 5° C. to about 100° C., preferably from about 25° to about 70° C.

The following non-limiting examples illustrate the invention.

EXAMPLE 1

Preparation of 2-methylthio-4-trifluoromethylbenzonitrile

Sodium thiomethoxide (366 g of a 21% aqueous solution, 1.1M) was added during 3 hours to a solution of 2-nitro-4- trifluoromethylbenzonitrile (220.5 g, 1.0M) in acetone (340 g) with stirring at 20–30° C. Stirring was continued for a further 1 hour and the two liquid phases separated. The upper layer (a solution of the product in acetone) was kept at 20° C. when 2-methylthio-4-trifluoromethylbenzonitrile crystallised (213 g), m.p.82° C. The yield was 97%, with product purity >96%.

EXAMPLE 2

Methanethiol (278 g, 5.78M) was added during 20 minutes to a stirred mixture of acetone (5 litres) and potassium carbonate (593 g, 4.29M) at −15° C. A solution of 2-nitro-4-trifluoromethylbenzonitrile (618 g, 2.86M) in acetone (500 ml) was added during 10 minutes. The mixture was allowed to warm to 20° C. with stirring for 23 hours and then heated at 55° C. for 2 hours to remove most of the methanethiol and then flushed with nitrogen for 4 hours. The mixture was poured onto ice/water, the solid filtered off, washed and dried to give 2-methylthio-4-trifluoromethylbenzonitrile (550 g). The yield of product was 89%.

EXAMPLE 3

Sodium thiomethoxide (37 g of a 21% aqueous solution, 0.11M) was added during 2 hours to a solution of 2-chloro-4-trifluoromethylbenzonitrile (20.56 g, 0.099M) in acetone (34 g) with stirring at 30–35° C. After a further 2.5 hours at 30–35° C. and 3 hours at 60° C., a further addition of sodium thiomethoxide (3.4 g of a 21% aqueous solution, 0.01M) was made. The mixture was maintained at 60° C. for 2 hours, cooled and the organic phase evaporated to give 2-methylthio-4-trifluoromethylbenzonitrile (20.3 g), m.p.80° C. The yield of product was 91%, with a purity of 97%.

Compounds of formulae (II) and (III) and processes for their preparation are known or may be prepared by known methods. Both the compounds of formula (I) above and the herbicidally active compounds which they may be used to prepare are described in the literature, for example in European Patent Publication Nos. 0418175, 0527036, or WO/9500476.

What is claimed is:

1. A process for the preparation of a compound of formula (I):

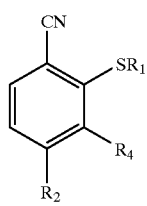

(I)

wherein
  $R_1$ represents $C_{1-6}$ alkyl;
  $R_2$ represents $C_{1-6}$ haloalkyl, $C_{1-6}$ alkyl, $C_{1-6}$ haloalkoxy, $C_{1-6}$ alkoxy, $SO_nR_5$ or halogen;
  $R_4$ represents hydrogen, $C_{1-6}$ haloalkoxy, $C_{1-6}$ alkoxy, $SO_nR_5$ or halogen; or a 5 or 6-membered heterocyclic ring which may be unsaturated or partially saturated having 1 to 3 hetero atoms selected from oxygen, nitrogen and sulphur, optionally substituted by halogen, $C_{1-6}$ haloalkyl, $C_{1-6}$ alkyl, $C_{1-6}$ haloalkoxy, $C_{1-6}$ alkoxy, $SO_nR_5$, nitro or cyano;
  $R_5$ represents $C_{1-6}$ alkyl; and
  n represents 0, 1 or 2;
which comprises reacting a compound of formula (II):

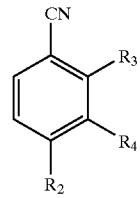

(II)

wherein $R_2$ and $R_4$ are as hereinbefore defined and $R_3$ represents nitro or a halogen atom selected from fluorine, chlorine and bromine, with a compound of formula $R_1S$—X,
wherein $R_1$ is as hereinbefore defined and X is hydrogen or an alkali metal, in a solvent selected from ethers, amides, sulphoxides, and ketones or mixtures thereof, optionally in the presence of water.

2. A process according to claim 1 in which $R_1$ represents $C_{1-6}$ alkyl; $R_2$ represents $C_{1-6}$ haloalkyl; and $R_4$ represents hydrogen.

3. A process according to claim 1 in which $R_1$ represents methyl, $R_2$ represents trifluoromethyl and $R_4$ represents hydrogen.

4. A process according to claim 1 in which $R_3$ represents nitro or chlorine.

5. A process according to claim 1 in which X represents a sodium, potassium or lithium atom.

6. A process according to claim 1 in which the molar ratio of the compound of formula (II): compound of formula $R_1$S—X is from about 1:1 to about 1:4.

7. A process according to claim 6 in which the molar ratio of the compound of formula (II): compound of formula $R_1$S—X is from about 1:1 to about 1:2.5.

8. A process according to claim 1, in which the solvent is a ketone optionally in the presence of water.

9. A process according to claim 1 in which the solvent is methyl ethyl ketone or acetone optionally in the presence of water.

10. A process according to claim 1 in which the solvent is acetone optionally in the presence of water.

11. A process according to claim 1 in which the solvent is acetone in the presence of water.

* * * * *